US010299862B2

United States Patent
Georgescu et al.

(10) Patent No.: US 10,299,862 B2
(45) Date of Patent: May 28, 2019

(54) THREE-DIMENSIONAL QUANTITATIVE HEART HEMODYNAMICS IN MEDICAL IMAGING

(71) Applicant: Siemens Healthcare GmbH, Erlangen (DE)

(72) Inventors: Bogdan Georgescu, Plainsboro, NJ (US); Lucian Mihai Itu, Brasov (RO); Ali Kamen, Skillman, NJ (US); Tommaso Mansi, Plainsboro, NJ (US); Viorel Mihalef, North Brunswick, NJ (US); Tiziano Passerini, Plainsboro, NJ (US); Rapaka Saikiran, Pennington, NJ (US); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 435 days.

(21) Appl. No.: 15/016,442

(22) Filed: Feb. 5, 2016

(65) Prior Publication Data
US 2016/0228190 A1    Aug. 11, 2016

Related U.S. Application Data

(60) Provisional application No. 62/112,382, filed on Feb. 5, 2015.

(51) Int. Cl.
*A61B 8/00*    (2006.01)
*A61B 8/06*    (2006.01)
(Continued)

(52) U.S. Cl.
CPC .............. *A61B 34/10* (2016.02); *A61B 5/022* (2013.01); *A61B 5/026* (2013.01); *A61B 8/065* (2013.01);
(Continued)

(58) Field of Classification Search
CPC ......... A61B 5/026; A61B 34/10; A61B 5/022; A61B 8/065; A61B 8/461;
(Continued)

(56) References Cited

U.S. PATENT DOCUMENTS

2012/0041739 A1* 2/2012 Taylor ................ A61B 5/02007
703/11
2013/0197884 A1* 8/2013 Mansi ..................... G06T 19/00
703/2

OTHER PUBLICATIONS

[Ionasec et al., 2010] Ionasec, Razvan Ioan, et al. "Patient-specific modeling and quantification of the aortic and mitral valves from 4-D cardiac CT and TEE." Medical Imaging, IEEE Transactions on 29.9 (2010): 1636-1651.
(Continued)

*Primary Examiner* — Hien N Nguyen (57) ABSTRACT

A medical system is provided for three-dimensional hemodynamic quantification. Comprehensive three-dimensional (3D) plus time (3D+t) assessment of flow patterns inside the heart are provided by a combination of lumped-parameter modeling and computational flow dynamic modeling. Using medical scanning, the lumped parameter model is personalized to a given patient. The personalized lumped-parameter model provides pressure curves (i.e., pressure as a function of time) for one or more locations. Using geometry of the patients heart segmented from the medical scanning and the pressure curves as boundary conditions, the computational flow dynamics model calculates the absolute pressure for any location (e.g., for a three-dimensional field of locations) in the patient heart at any one or more phases of the cardiac cycle. More accurate absolute pressure may be provided without invasive measurement.

19 Claims, 6 Drawing Sheets

(51) Int. Cl.
*A61B 8/08* (2006.01)
*G06T 7/00* (2017.01)
*A61B 34/10* (2016.01)
*A61B 5/022* (2006.01)
*A61B 5/026* (2006.01)
*G16H 50/50* (2018.01)

(52) U.S. Cl.
CPC .......... *A61B 8/5223* (2013.01); *G06T 7/0012* (2013.01); *G16H 50/50* (2018.01); *A61B 8/461* (2013.01); *A61B 2034/105* (2016.02); *G06T 2207/10132* (2013.01); *G06T 2207/30048* (2013.01); *G06T 2207/30104* (2013.01)

(58) Field of Classification Search
CPC ... A61B 2034/105; A61B 8/5223; A61B 8/00; A61B 8/06; G16H 50/50; G06T 2207/30048; G06T 2207/30104; G06T 7/0012; G06T 2207/10132; G06T 7/00; A61N 1/36528; G06F 19/00
See application file for complete search history.

(56) References Cited

OTHER PUBLICATIONS

Itu, Lucian, et al. "Model based non-invasive estimation of PV loop from echocardiography." Engineering in Medicine and Biology Society (EMBC), 2014 36th Annual International Conference of the IEEE. IEEE, 2014.

Itu, Lucian, et al. "Non-invasive hemodynamic assessment of aortic coarctation: validation with in vivo measurements." Annals of biomedical engineering 41.4 (2013): 669-681.

Mihalef, Viorel, et al. "Patient-specific modelling of whole heart anatomy, dynamics and haemodynamics from four-dimensional cardiac CT images." Interface Focus 13 (2011): 286-296.

Mynard, J. P., et al. "A simple, versatile valve model for use in lumped parameter and one-dimensional cardiovascular models." International journal for numerical methods in biomedical engineering 28.6-7 (2012): 626-641.

Nocedal et al., Nocedal, J., Wright, S. J. "Numerical Optimization", Springer, New York, NY, USA, 2006.

Scutaru, Mihai, et al. "Robust Detection of Mitral Papillary Muscle from 4D Transesophageal Echocardiography." Statistical Atlases and Computational Models of the Heart-Imaging and Modelling Challenges. Springer International Publishing, 2015. 249-256.

Segers, Patrick, et al. "Systemic and pulmonary hemodynamics assessed with a lumped-parameter heart-arterial interaction model." Journal of Engineering Mathematics 47.3-4 (2003): 185-199.

Shroff, Sanjeev G., Joseph S. Janicki, and Karl T. Weber. "Evidence and quantitation of left ventricular systolic resistance." American Journal of Physiology-Heart and Circulatory Physiology 249.2 (1985): H358-H370.

Stergiopulos, Nikos, Berend E. Westerhof, and Nico Westerhof. "Total arterial inertance as the fourth element of the windkessel model." American Journal of Physiology-Heart and Circulatory Physiology 276.1 (1999): H81-H88.

[Suga, 1974] Suga H., Importance of Atrial Compliance in Cardiac Performance, Circulation Research, 1974; 35: 39-43.

Voigt, Ingmar, et al. "Patient-specific model of left heart anatomy, dynamics and hemodynamics from 4D TEE: a first validation study." Functional Imaging and Modeling of the Heart. Springer Berlin Heidelberg, 2011. 341-349.

Wang, Yang, et al. "Automatic cardiac flow quantification on 3D volume color Doppler data." Biomedical Imaging: From Nano to Macro, 2011 IEEE International Symposium on. IEEE, 2011.

Wang, Yang, et al. "Volumetric myocardial mechanics from 3D+ t ultrasound data with multi-model tracking." Statistical Atlases and Computational Models of the Heart. Springer Berlin Heidelberg, 2010. 184-193.

Westerhof, Nicolaas, et al. "Analog studies of the human systemic arterial tree." Journal of biomechanics 2.2 (1969): 121-143.

* cited by examiner

Left heart CFD setup

Personalized pressures
are used as
boundary conditions

THREE-DIMENSIONAL QUANTITATIVE HEART HEMODYNAMICS IN MEDICAL IMAGING

RELATED APPLICATIONS

The present patent document claims the benefit of the filing date under 35 U.S.C. § 119(e) of Provisional U.S. Patent Application Ser. No. 62/112,382, filed Feb. 5, 2015, which is hereby incorporated by reference.

BACKGROUND

The present embodiments relate to medical assessment of heart function. Heart function is assessed with any of a variety of imaging modalities and/or signals obtained by external scanning or measurements. Pressure, pressure-volume loops in particular, has been shown to characterize cardiac function and the efficiency of pump function. However, intra-cardiac pressure measurement requires invasive examination where a pressure catheter is inserted into the cavity.

Imaging may be used to obtain some pressure information. Flow imaging (e.g. Color Doppler ultrasound or phase-contrast magnetic resonance imaging (MRI)) is a common surrogate, enabling the computation of pressure gradients. Yet, the images or scan data used to compute pressure gradients have sources of inaccuracy, such as being unidirectional (ultrasound-based) or being planar (2D PC-MRI) instead of including a three-dimensional pressure or having poor spatial and/or temporal resolution (3D PC-MRI). Furthermore, flow provides only information on pressure gradient (e.g. pressure drop across a valve), but not the absolute pressure. On the other hand, invasive pressure and pressure-volume measurements are sensitive to the position of the catheter inside the heart and to noise.

BRIEF SUMMARY

By way of introduction, the preferred embodiments described below include methods, computer readable media, and systems for three-dimensional hemodynamic quantification in a medical system. Comprehensive three-dimensional (3D) plus time (3D+t) assessment of flow patterns inside the heart are provided by a combination of lumped-parameter modeling and computational flow dynamic modeling. Using medical scanning, the lumped parameter model is personalized to a given patient. The personalized lumped-parameter model provides pressure curves (i.e., pressure as a function of time) for one or more locations. Using geometry of the patients heart segmented from the medical scanning and the pressure curves as boundary conditions, the computational flow dynamics model calculates the absolute pressure for any location (e.g., for a three-dimensional field of locations) in the patient heart at any one or more phases of the cardiac cycle. More accurate absolute pressure may be provided without invasive measurement.

In a first aspect, a method is provided for three-dimensional hemodynamic quantification in a medical system. A medical scanner of the medical system captures cardiovascular spatial data and flow data of a heart of a patient. The spatial and flow data represents a three-dimensional volume. A pressure sensor of the medical system measures pressure data of the patient. A three-dimensional representation of the portion of the heart is generated from the spatial data. Flow across valves of the heart is estimated from the flow data. A lumped-parameter hemodynamics model representing at least a portion of the heart of the patient is personalized where the personalizing uses the spatial data, the flow across the valves, and the pressure data. A hemodynamic parameter is quantified from computational flow dynamics using the three-dimensional representation and using the lumped-parameter hemodynamics for a boundary condition. The quantifying provides a three-dimensional distribution of the hemodynamic parameter for the portion. A metric is indicated on a display for the patient. The metric is a function of the quantifying of the hemodynamic parameter.

In a second aspect, a non-transitory computer readable storage medium has stored therein data representing instructions executable by a programmed processor for three-dimensional hemodynamic quantification in a medical system. The storage medium includes instructions for modeling, by a first part of the medical system, pressure over time for a part of a heart of a patient with a lumped-parameter model personalized to the patient, solving, by a second part of the medical system, for hemodynamics of the heart of the patient with a three-dimensional computational flow dynamics model personalized to the part of the heart, applying, based on communication between the first and second parts of the medical system, the pressure over time from the modeling with the lumped-parameter model as a boundary condition in the solving with the three-dimensional computational flow dynamics model, and transmitting, to a memory or display, a value for the hemodynamics resulting from the solving.

In a third aspect, a medical system is provided for three-dimensional hemodynamic quantification. A scanner is configured to scan a heart of a patient. A memory is configured to store clinical measurements of the patient. A model system is configured to segment heart geometry, fit a lumped-parameter model to the heart of the patient with a measurement from the segmented heart geometry, the clinical measurements, and flow measurements from the scan, and compute a biomarker quantity with a three-dimensional computed flow dynamics model with the segmented heart geometry and information from the fit lumped-parameter model as boundary conditions.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Anatomical and flow scan data are used for non-invasive quantification of pressure, volume, and/or 3D hemodynamics of the heart. The ventricular pressure-volume loop, as well as ventricular velocities, is estimated from medical images of cardiac anatomy and blood flow (e.g. ultrasound Doppler, MRI) and non-invasive cuff pressure measurements. Imaging is combined with computational modeling and routine clinical measurements (e.g., heart rate and cuff pressures) to provide cardiac hemodynamic parameters like pressure-volume (PV) loop, 3D pressure field biomarkers (e.g. stress on valves), and 3D velocity field or map of biomarkers (e.g. apical residence time). Since pressure and/or flow information are provided throughout the heart, localized assessment may be made. Measurements that are nowadays not accessible in clinical routine may be made.

In one embodiment, a fast-personalization lumped-parameter hemodynamics (LPH) model for the left side circulatory system (e.g., pulmonary veins, left heart, and systemic circulation) is combined with a full 3D+time left heart hemodynamics circulation engine. The LPH model is used as boundary condition generator. The LPH model computes the left ventricular PV loop, while the computational flow dynamics (CFD) model uses the segmented geometry and the LPH provided pressure curves to generate 3D+time velocity and/or pressure maps inside the left ventricle. Parameters based on the PV loop, 3D pressure, and the 3D velocity may be provided to the user as additional biomarkers for disease assessment.

In another embodiment, the left heart ventricle and valves are segmented from scan data from a patient. Flow across valves is estimated from 3D flow images (e.g. PC-MRI or Doppler ultrasound). A LPH model for the left side circulatory system (e.g., including pulmonary veins, left heart, and systemic circulation) is personalized to the patient. The left ventricular PV-loop is computed and displayed using the LPH model. 3D+time left heart hemodynamics (e.g., time and space dependent velocities and pressures) are computed using the LPH model and the segmented geometry to enforce patient-specific boundary conditions. Advanced hemodynamics-based biomarkers may be computed and visualized.

Accurate, comprehensive, but non-invasive, assessment of cardiac hemodynamics, including absolute pressure and 3D hemodynamics patterns, is provided. This quantification may impact clinical findings and treatment planning, for example, due to the concurrent availability of both patient specific pressures and velocities inside the heart. The assessment may be used for diagnosis where the computed PV loop and hemodynamic information is provided to the clinician for decision making. The assessment may be used for predictive modeling or disease monitoring where the estimated parameters are used for advanced physiological measurements (e.g. apical residence time) to assess disease state and progression. The assessment may be used for therapy planning (e.g. model-based prediction of cardiac resynchronization therapy).

Figure 1:
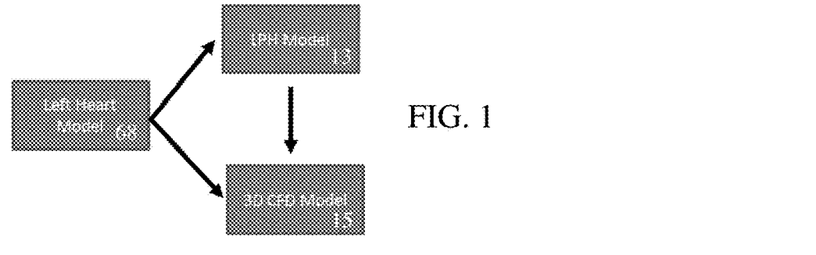
FIG. 1 is a block diagram representing a modeling system for three-dimensional hemodynamic quantification in a medical system.

FIG. 1 illustrates the general medical system and corresponding workflow according to one embodiment. A left heart model is formed for a particular patient. Other portions of the heart may be included or provided instead of the left heart (e.g., right heart or whole heart). The left heart example is used herein. The left heart model is a geometrical representation of the left heart. A mesh representing the left heart over time is extracted from a medical scan of the patient.

The segmented heart model provides mean measurements used by the LPH model and provides the complete left ventricular geometry used as a boundary condition by the 3D CFD model. Additional, different, or less information may be provided to either or both of the LPH and CFD models. The LPH model uses Windkessel models for venous and systemic circulations, coupled with resistance-inertance models for valves and elastance-based models for left atrial and ventricular chambers. Other lumped representations may be used in all or parts of the LPH. The LPH model is personalized from the flow measurements (e.g. Color Doppler, PW-or CW-Doppler) as well as from routine clinical measurements, but may be personalized based on different, additional, or less information.

The 3D CFD model is coupled with the LPH model. The LPH model provides boundary condition information that is not directly available in the 3D CFD model. For example, the pressure, velocity, or other information is provided from the LPH model for one or more locations. Using the LPH information as a boundary condition in the CFD model allows the 3D CFD to perform personalized computations not otherwise available or to provide more accurate computations.

Figure 2:
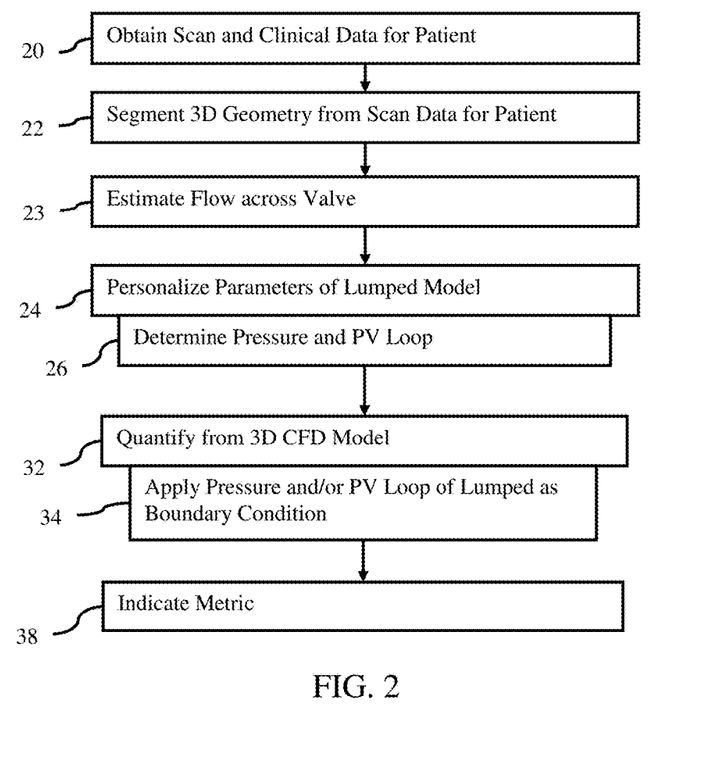
FIG. 2 is a flow chart diagram of one embodiment of a method for three-dimensional hemodynamic quantification in a medical system.

FIG. 2 shows a method for three-dimensional hemodynamic quantification in a medical system. The method is implemented by the medical system, such as a medical diagnostic imaging system, a review station, a workstation, a computer, a picture and archiving and communications system (PACS) station, a server, combinations thereof, or other device for image processing medical scan data. For example, the medical system, computer readable media, and/or model system shown in FIG. 10 implements the method, but other medical systems may be used.

The method is implemented in the order shown or a different order. For example of different order, act 23 is performed prior to act 22. Additional, different, or fewer acts may be performed. For example, act 22 is not performed where the personalization operates on the image data without segmentation. In another example, acts for storing scanned data and/or transfer of results are provided. In yet another example, act 38 is not provided.

The acts are performed in real-time, such as during a surgical procedure. Performing during the procedure allows the clinician to diagnose and/or treat based on information computed from the scan data to assist an on-going procedure. In other embodiments, the acts are performed after a procedure (e.g., performing as part of a review), as part of diagnosis, or before a procedure for planning. The method may be repeated to provide comparative information over time.

Some (e.g., all but act 20) or all of the acts are performed automatically by the model system. The user causes the patient to be scanned or obtains scan data for the patient from a previous scan. The user may activate the process and input patient-specific information, such as a metric of interest, age, sex, and/or weight. Once personalization and/or metric computation are activated, the method is performed without any user input, such as without user input of locations and/or values. Alternatively, the user assists in a semi-automated process, such as the user indicating possible values of properties. Other user input may be provided, such as for changing modeling parameter values, correcting output, and/or to confirm accuracy.

In act 20, data representing a patient is obtained. One or more of different types of data are obtained. For example, data from a computerized medical record is obtained, such as diagnosis, age, weight, and sex. In one embodiment, scan and clinical data are obtained. The clinical data may be ECG measurements measured with electrodes and an ECG sensor. The clinical data may be pressure data measured with a pressure cuff of the medical system, but internal pressures may instead or additionally be measured with a pressure sensor on a catheter. Other clinical data may be obtained.

The scan data is image data or data representing different locations measured with a medical diagnostic scanner, such as an ultrasound, computed tomography, x-ray, fluoroscopy, angiography, or magnetic resonance scanner. Any scanning sequence or approach may be used. The scan data is cardiovascular spatial data, such as B-mode data representing tissue response of the heart or part of the heart captured with an ultrasound scanner. The scan data may alternatively or additionally be flow data, such as color Doppler data captured by an ultrasound scanner and representing velocity, power, and/or variance of flow in the heart or part of the heart. Other types of data may be obtained.

The data is obtained at a same time, such as measuring pressure while also scanning. Alternatively, the data is obtained at different times, such as in sequence during a single patient visit or appointment or in sequence across hours or days.

The data is acquired by scanning and/or measuring the patient. In an alternative embodiment, the data is acquired by loading from memory. Data from a previously performed scan of the patient is stored in a memory, such as a picture archiving and communications system (PACS) database. The data is selected from the database. The data may be obtained by transfer, such as over a network or on a portable memory device.

The scan data represents a volume. The scan data is organized or formatted as a frame, set of data, sets of data, or other collection to represent the volume. The scan data represents locations distributed in three dimensions. The volume includes the heart and one or more vessels. Only a portion of the heart may be imaged in other embodiments.

Scan data of the volume over time is acquired. Any temporal resolution may be provided. Similarly, the clinical data includes measures over time with the same or different temporal resolution as the scan data. Data for just one time or from a combination of times may be acquired.

In act 22, a processor segments the cardiovascular spatial data for a heart or part of the heart of the patient. Scan data representing the heart within a three-dimensional volume of the patient represented in the cardiovascular spatial data is identified. Using thresholding, edge detection, contrast detection, shape fitting, flow detection, combinations thereof, or other process, locations associated with the part or all of the heart or other cardiovascular part as compared to other anatomy are identified. The type of scanning or detection may result in acquiring data from the cardiovascular system and no other anatomy, such as by contrast detection and/or flow detection. The heart may be represented as tissue of the heart walls, the boundary of the tissue with blood, and/or the exterior of the blood column.

To allow for calculation of change or variation through the cardiac cycle, the locations for cardiac structure (e.g., heart chambers) are segmented in at least two phases of a cardiac cycle. The scan data is acquired for each of the phases (e.g., end diastole and end systole). The scan data for each phase is segmented to provide the anatomy at the different times in the cycle.

The medical system generates a three-dimensional representation of the left side of the heart from the spatial data. A mesh personalized to the patient is created. The 3D ultrasound spatial data (e.g., B-mode or tissue representation) is processed to estimate a four-dimensional (3D+t) model of the left heart.

Figure 3:
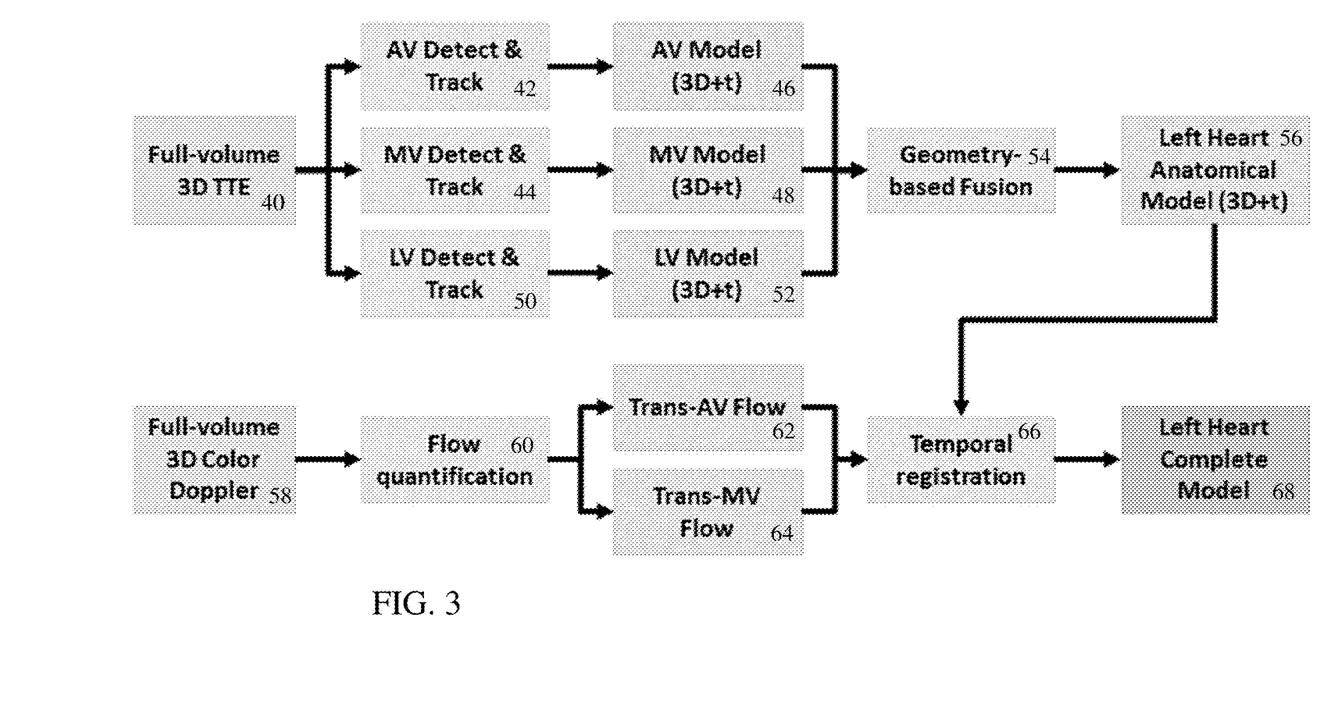
FIG. 3 illustrates creating of a geometrical representation of a portion of a heart and measurement of flow for that portion.

In one embodiment, different parts of the left heart are separately segmented and then the meshes for the different parts are fused together into a mesh for the larger portion. FIG. 3 shows one embodiment of a method for separate segmentation and fusion used in creating the personalized left heart model 68 of FIG. 1.

The separate parts are the left ventricle, aortic valve (AV), mitral valve (MV), and the anterior and posterior papillary muscles. Additional, different, or fewer parts may be separately segmented. Each part is segmented independently and then fused together to form a unified left heart model, but dependent segmentation may be used. The segmentation in the example of FIG. 3 is from a transthoracic ultrasound scan (TTE) of the left heart 40, but other scans may be used (e.g., transesophageal).

Figure 4:
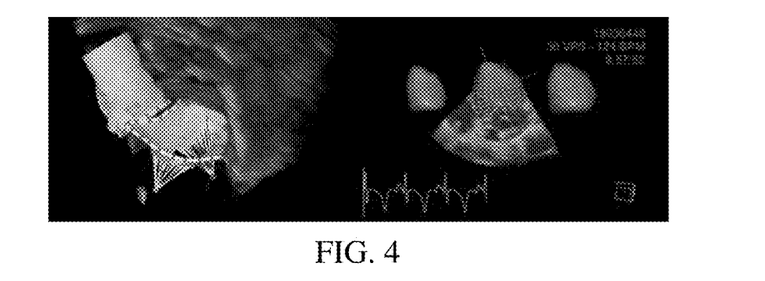
FIG. 4 shows example images with segmentation of valves and left ventricle.

Any segmentation may be used. In one embodiment, the aortic and mitral valves are detected in acts 42 and 44 following a marginal space learning (MSL) approach. A box around each valve, defined by location, orientation, and size of each valve, is detected using probabilistic boosting trees trained on a large database of annotated images. This defines a box around each valve, within which anatomical landmarks are detected using the same machine-learning framework. Example landmarks may be two MV trigones, midpoint of posterior MV annulus, two MV commissures, two MV leaflet tips, two papillary tips, three AV hinges, three AV commissures, three AV leaflet tips. Additional, different, or fewer landmarks may be used. A mean shape model of the mitral valve leaflets, aortic root and aortic valve leaflets is then warped to fit the landmarks and automatically deformed under shape-constraint to match the boundaries visible in the images. FIG. 4 shows example segmented aortic and mitral valves with fitted meshes on the left side. The fitted meshes are aortic and mitral valve models 46, 48.

The left ventricle is automatically segmented in act 50 in a similar or different way. For example, the global position, orientation, and size of the left ventricular endocardium (LV) are detected using MSL and probabilistic trees. A mean LV model is then mapped to the detected region, and deformed within the shape-space learned from the annotated database according to boundary forces driven by steerable features. The LV model 52 is provided. FIG. 4 shows an example segmented left ventricle with a fitted mesh. The arrow shows estimated deformation from fitting to the ultrasound spatial data.

For temporal segmentation, the models are created for each cardiac phase. Alternatively or additionally, the cardiac structure from one phase with the fitted model is tracked to other phases and the identified deformation is applied to the fitted model. In one embodiment, a 4D valve model as well as a 4D LV geometric model are obtained by using collaborative trackers, which are algorithms that fuse constraints obtained from several types of tracking information based on (but not limited to) learned motion manifolds, speckle tracking, optical flow registration, shape models, kinematic motion models imposing periodic motion, and/or other approaches.

In act 54, the separately segmented models 46, 48, 52 are combined to form a geometry-based fusion of cardiac structures of the left heart. At each time frame of the sequence, the AV, MV and LV models 46, 48, 52 are fused together in a watertight surface model 56 for subsequent hemodynamics computation. An energy minimization with smoothness and/or continuity constraints is used to combine the meshes so that holes do not result where there are no anatomical holes. As all models derive from a mean shape model, their parameterization (i.e., the way the triangles and vertices are defined per model) is consistent over time and over patients. The vertices at the edges of each model are connected together. The LV model connects with the posterior MV annulus and half of the AV annulus, MV anterior annulus, and AV annulus, creating the aortic-mitral curtain. Other connections may be used. Generic papillary muscles may also be created based on the papillary tip position. Because the sampling is identical among patients, the connections may be implemented programmatically.

Figure 5:
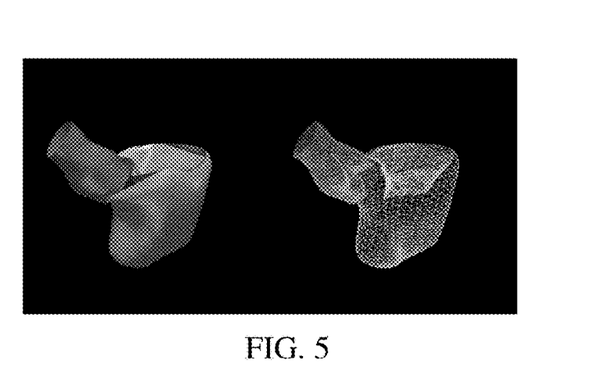
FIG. 5 shows example fusing of separately tracked geometrical information for the heart.

FIG. 5 shows an example fused mesh as the left heart anatomical model 56. The left heart anatomical model 56 is a geometric model representing the heart at any number of phases (e.g., a 3D+t model).

Referring to FIG. 2, the medical system estimates flow across one or more valves of the heart from the flow data in act 23. In the left heart embodiment, the flows across the atrial valve and mitral valve are estimated. Scan data, such as the flow or color Doppler ultrasound data, is used to quantify trans-aortic and trans-mitral flow for subsequent model estimation.

The estimated flow is the flow rate. Any flow may be estimated, such as the volume flow and/or velocity of flow. In the embodiment of FIG. 3, trans-valvular flow estimation of act 60 is from Color Doppler trans-valvular flow information or from full-volume, real-time 3D Color Doppler images or scan data 58. The AV and MV are detected and tracked in the Color Doppler images, such as detecting and tracking using the associated B-mode data as described above for acts 42 and 44. The valve models 46, 48 are used to define the valve planes through which flow is to be quantified. Once defined, the trans-AV and MV flows 62, 64 are calculated.

To cope with any aliasing of the Doppler data, instantaneous volume changes are calculated by segmenting and tracking the LV boundaries. The volume change indicates a maximum velocity, allowing antialiasing. Any detection and/or tracking in Doppler or flow scan data may be used for detecting volume change, such as identifying regions of expected flow variation and/or velocity thresholding. If the LV is not available in the Doppler image, the LV volume curve measured from the anatomical images, such as using the detection of act 50 and LV model 52, is used assuming constant heart rate. Since the B-mode and Doppler data are obtained interleaved with each other, this approach does not need further registration with anatomical model data. Other anti-aliasing may be used. Alternatively, the Doppler data is assumed to be unaliased.

In act 66, the left heart anatomical model 56 is temporally registered with the valve flow 62, 64. Where the valve flow 62, 64 and anatomy are based on a same scan, such as interleaving scan, then the results are temporally registered. In other embodiments, interpolation or other technique is used to temporally register the cardiac cycle associated with the anatomy model 56 with the cardiac cycle associated with the valvular flow 62, 64. The registered anatomical and flow provide a left heart complete model 68.

The left heart complete model 68 may be used for quantifying flow and/or anatomy for the left heart of the patient. Any measurements may be used. For example, time-varying LV volume variation, LV myocardium strain, trans-valvular flow 62, 64, aortic leaflets and annulus area, mitral valve leaflet and annulus area, aortic valve orifice area, and mitral valve orifice area are calculated.

As shown in FIG. 1, the left heart model 68 is used to create the LPH model 13. The lumped model 13 part of the medical system models the PV loop and/or pressure over time for a part of a heart of a patient with the LPH model personalized to the patient. The pressure over time or pressure curve may be used in the 3D CFD model 15 as a boundary condition. The personalized left circulation model (e.g., LPH) is coupled with the 3D CFD solver in order to provide variable pressure boundary conditions. Additional, different, or fewer hemodynamic parameters may be estimated by the LPH model 13, whether or not for use by the 3D CFD model 15.

Referring again to FIG. 2, the medical system personalizes the LPH model in act 24. The LPH represents at least a portion of the heart of the patient, but with a 0D representation. The heart, such as the left heart, is simplified or reduced in the lumped representation. Alternatively, a 1D or other reduced-order model may be used.

Figure 6:
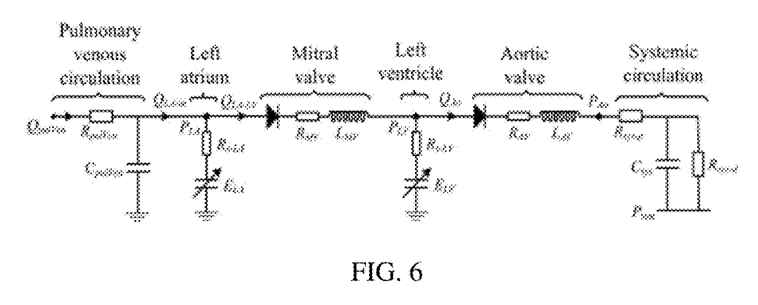
FIG. 6 illustrates one embodiment of a lumped-parameter hemodynamic model of the left side of the heart.

FIG. 6 shows one embodiment of the LPH model. The LPH model has three main components: venous pulmonary circulation, left side of the heart, and the systemic circulation, but more or fewer main components may be used. The LPH model represents the left circulation. The left heart model has four components: left atrium (LA), mitral valve, left ventricle (LV) and aortic valve, but may have more or fewer left heart components. P is pressure, Q is flow rate, "in" is inlet, Ao is aortic, pul is pulmonary, and ven is venous.

In the embodiment of FIG. 6, a time varying elastance model is used for the LA and the LV, personalized from volume curves and Doppler velocities, while the valve resistance and inertance parameters are personalized as well such that trans-valvular flow estimated from measured Doppler velocity curves is matched. A modified Heaviside or other switch-like function is used to enable regurgitation handling, and a three-element Windkessel or other model is used for the systemic circulation. Flow information (e.g., mitral and aortic flow) from flow imaging (e.g., Doppler scan data) may be used to provide extra constraints for model personalization. In other embodiments, different lumped and/or non-lumped (e.g., 3D) representations are used for any of the components.

In the embodiment of FIG. 6, the model system of the medical system personalizes pulmonary circulation as a pulmonary resistance and compliance with the flow data. For the venous part of the pulmonary circulation, a resistance ($R_{pulVen}$) and a compliance ($C_{pulVen}$) are used, as represented by:

$$C_{pulVen} \frac{dP_{LA}}{dt} = Q_{C-pulVen}; P_{pulVen} - P_{LA} = Q_{pulVen} \cdot R_{pulVen}; \quad (1)$$

$$Q_{pulVen} = Q_{C-pulVen} + Q_{LA-in}. \quad (2)$$

where $P_{LA}$ is the pressure in the left atrium, $P_{pulVen}$ is the pulmonary venous pressure, and the venous pulmonary flow rate ($Q_{pulVen}$) is considered to be constant in time. Other representations may be used.

The model for the left side of the heart includes four components: left atrium, mitral valve, left ventricle, and aortic valve. For heart chamber flow, the model system of the medical system personalizes a time varying elastance model with volume over time from the spatial data and velocity from the flow data. A time-varying elastance model is used for both the left atrium and the left ventricle, as represented by:

$$P(t)=E(t) \cdot (V(t)-V_0) \cdot (1-K_s Q(t)), \quad (3)$$

where E is the time-varying elastance, V is the cavity volume, $V_0$ is the dead volume (e.g., cavity at rest) of the cavity, and $K_s$ is a source resistance coefficient that accounts for the dependence between the flow and the cavity pressure. $K_s$ is set to a constant value, such as 4e-9 s/ml for the left ventricle. Alternatively, $K_s$ is estimated as in equation 16 if extra information is provided. Other representations may be used.

The volume for the cavities (e.g., atrium and ventricle) is computed as follows:

$$\frac{dV}{dt} = Q_{in} - Q_{out}, \quad (4)$$

where $Q_{in}$ represents the inlet flow rate into the cavity and $Q_{out}$ represents the outlet flow rate from the cavity. Other change in volume computations may be used, such as change in volume based on volume measures using the anatomical mesh or geometric heart model.

The model system of the medical system personalizes the valve resistance and inertance from the flow data. The mitral valve and the aortic valve are modeled using a laminar resistance (R), a Bernoulli resistance (B) and an inertance (L), as well as a diode to simulate the closure and the opening of the valve. For non-regurgitant cases, the following relationship holds:

$$(P_{in} - P_{out}) \cdot H(P_{in} - P_{out}) = R_{valve} \cdot Q + B_{valve} \cdot Q^2 + L_{valve} \cdot \frac{dQ}{dt}, \quad (5)$$

where $P_{in}$ and $P_{out}$ represent the pressures at the inlet and the outlet, respectively, of the valve, Q is the flow rate through the valve, and H is the Heaviside function. The use of the Heaviside or other switching function enforces the physical requirement that the pressure drives the opening of the valve, for example only if the pressure of the ventricle is larger than the pressure of the aorta. In this case, the Heaviside function is nonzero, and flow is generated through the valve. Other representations may be used.

For regurgitant cases, the formulation is extended by using a modified Heaviside or switching function. The modification replaces the zero flow with regurgitant flow. The formula is $$(P_{in} - P_{out}) \cdot H_\varepsilon (P_{in} - P_{out}) = R_{valve} \cdot Q + + B_{valve} \cdot Q^2 + L_{valve} \cdot \frac{dQ}{dt}, \quad (6)$$

where the modified Heaviside function is defined as $$H_\varepsilon(x) = \begin{cases} 1, & x > 0 \\ \varepsilon, & x \leq 0 \end{cases}.$$

x is the pressure differential. The new formulation allows flow in both directions, with the appropriate sign, through the regurgitant valve. ε is a real number between 0 and 1 that represents regurgitation or relative defect and is defined by default to be the valve minimum orifice area divided by the maximum opening area. Other definitions may be used. The relative defect parameter ε may be further personalized based on the flow imaging data. Other representations than equation 6 and/or the modified Heaviside function may be used.

The model system of the medical system personalizes systemic circulation with a Windkessel model. A three-element Windkessel model is used for the systemic circulation, represented by the following relationship between instantaneous flow and pressure:

$$\frac{dP_{Ao}}{dt} = R_{sys-p} \frac{dQ_{Ao}}{dt} - \frac{P_{Ao} - P_{ven}}{R_{sys-d} \cdot C_{sys}} + \frac{Q_{Ao}(R_{sys-p} + R_{sys-d})}{R_{sys-d} \cdot C_{sys}}, \quad (7)$$

where $R_{sys-p}$ and $R_{sys-d}$ are the proximal and distal resistances respectively, and $C_{sys}$ is the compliance. Other representations may be used.

Nine equations are used for personalization, but other numbers of equations may be used. The nine equations include two for the venous pulmonary circulation, two for each heart cavity, one for each valve, and one for the systemic Windkessel model.

The equations are solved using the forward Euler time integration scheme. Other explicit or implicit numerical integration may be used for solving, such as Runge-Kutta. A two-stage approach to the personalization may be used. In a first stage, the values for one or more parameters are calculated from available measurements, such as direct calculation. In a second stage, the numerical solution or optimization is used to solve for the values of one or more other parameters. The optimization is automatic calibration. The personalization determines parameters of the LPH model that fits the LPH model to the data from the patient.

In one embodiment of the first stage, patient-specific input parameters are calculated. The mean arterial pressure is calculated from the pressure data, and the ejection fraction and end-diastolic volume are calculated from the spatial and/or flow data. Some (e.g., a sub-set) of the parameters of the LPH model are calculated from the mean arterial pressure, ejection fraction, and end-diastolic volume. Any of the calculations may use any of the types of available data for the patient. The spatial data, such as in the form of the geometric or anatomical model 68, the flow across the valves, and pressure data (e.g., from the cuff) are used for the personalization. Additional, different, or fewer types of data may be used.

Table 1 shows the patient-specific input parameters of this embodiment.

TABLE 1

List of patient-specific input parameters.

| Input | Source |
|---|---|
| Systolic blood pressure (SBP) | Cuff measurement (arms) |
| Diastolic blood pressure (DBP) | Cuff measurement (arms) |
| Heart Rate (HR) | Routine measurement |
| Ejection fraction (EF) | Echocardiography |
| End-diastolic volume (EDV) | Echocardiography |

The mean arterial pressure (MAP) is determined as:

$$MAP = DBP + \left[\frac{1}{3} + (HR \cdot 0.0012)\right] \cdot (SBP - DBP). \quad (8)$$

Then, the end-systolic volume is computed as:

$$ESV = EDV \cdot \frac{1 - EF}{100.0}. \quad (9)$$

Next, the stroke volume is determined as:

$$SV = EDV - ESV, \quad (10)$$

and the average aortic flow rate is computed as:

$$\overline{Q_{Ao}} = \frac{SV \cdot 60}{HR}. \quad (11)$$

Finally, the total systemic resistance and the proximal and distal components of the total are determined as:

$$R_t = \frac{MAP - P_v}{\overline{Q}} \quad (12)$$

$$R_p = \rho \cdot R_t$$

$$R_d = (1 - \rho) \cdot R_t$$

where $\rho$ is the proximal resistance fraction (e.g., population average or extracted as a personalized parameter from pressure or flow information). $\rho$ may be tuned as discussed for equations 15 or 16 in other embodiments. The mean arterial pressure may be introduced, where the reference value of the mean arterial pressure may be computed as provided in equation 8. $P_v$ is the venous pressure and may be based on a population average and/or feedback from the 3D CFD model.

Since the lumped model is used to perform a pulsatile steady-state computation, the average inlet flow rate into the model ($Q_{pulVen}$) is equal to the average outlet flow rate, given by equation 11. Hence:

$$Q_{pulVen} = \overline{Q_{Ao}} \quad (13)$$

The normalized elastance curve (e.g., population average) is used for the left ventricle model, which is denormalized to account for difference in heart cycle timing and maximum elastance of the patient as compared to the population average. The curve is denormalized using the minimum elastance value, the maximum elastance value, and the time at which the maximum elastance is reached. The minimum elastance value is set to 0.08 mmHg/ml, and the time at which the maximum elastance of the left ventricle is reached is computed using:

$$t_{max} = 0.16 \cdot T + 0.17 \quad (14)$$

where T is the period. The maximum elastance value is estimated in the second stage as a numerical optimization. The maximum elastance is not used during the direct calculation. The denormalized elastance curve is used during the second stage of the personalization methodology. A two-hill function is used to determine the elastance curve for the left atrium, whereas the minimum elastance is set to 0.08 mmHg/ml, the maximum elastance is set to 0.17 mmHg/ml, and the onset of the contraction is set at 0.85 T.

Other equations or calculations may be used for any of the sub-set of parameters solved by direct calculation from the data. Different, additional, or fewer parameters may be used for direct calculation of the values in personalization.

In the second stage, the remaining parameters (i.e., second sub-set) are solved or calibrated. To personalize, the model system calibrates the LPH with an optimization. In one embodiment where only the anatomical imaging or scan data is available, the maximum elastance of the left ventricle model, $E_{max-LV}$, the dead volume of the left ventricle, $V_{0-LV}$, and the compliance of the systemic Windkessel model, $C_{sys}$, are estimated with numerical solution. In another embodiment where the flow imaging or scan data is also available, the flow data provides mitral and aortic velocities. Using the valve orifice area, flow through the valve is computed and used to estimate two extra parameters, for example $Ks_{\_LA}$ and $K_{s\_LV}$. Additional, different, or fewer extra parameters may be computed. In the special case when any of the valves are regurgitant, the relative defect parameter, $\varepsilon$, may be personalized through calibration.

The parameter estimation problem is formulated as a numerical optimization problem, the goal of which is to find a set of parameter values for which a set of objectives are met. Since the number of parameters to be estimated is set equal to the number of objectives, the parameter estimation problem becomes a problem of finding the root for a system of nonlinear equations. To solve the system of equations, the dogleg trust region method is used, but other solutions may be used. The objectives of the parameter estimation method are formulated in option 1 based on the systolic and diastolic pressures, and on the ejection fraction. Hence, the system of nonlinear equations is formulated as follows:

$$r\begin{pmatrix} E_{max-LV} \\ V_{0-LV} \\ C_{sys} \end{pmatrix} = \begin{Bmatrix} (SBP)_{comp} - (SBP)_{ref} \\ (DBP)_{comp} - (DBP)_{ref} \\ (EF)_{comp} - (EF)_{ref} \end{Bmatrix} = \begin{Bmatrix} 0 \\ 0 \\ 0 \end{Bmatrix} \quad (15)$$

where r(x) is a vector function, called in the following objective function, and x is the vector of the unknowns (i.e., the parameters to be estimated). Each component of the objective function is formulated as the difference between the computed value of a quantity—$(\bullet)_{comp}$ determined using the lumped parameter model, which is parameterized with the current set of parameter values and its reference value— $(\bullet)_{ref}$ determined through measurement. Note that, to evaluate the objective function for a given set of parameter values, the lumped parameter model is run once, but may be run any number of times. Other formulations and/or objective functions may be used.

In option 2, the system is expanded to the following:

$$r \begin{pmatrix} E_{max\text{-}LV} \\ V_{0\_LV} \\ C_{sys} \\ Ks\_LA \\ Ks\_LV \end{pmatrix} = \begin{Bmatrix} (SBP)_{comp} - (SBP)_{ref} \\ (DBP)_{comp} - (DBP)_{ref} \\ (EF)_{comp} - (EF)_{ref} \\ (MF)_{comp} - (MF)_{ref} \\ (AF)_{comp} - (AF)_{ref} \end{Bmatrix} = \begin{Bmatrix} 0 \\ 0 \\ 0 \\ 0 \\ 0 \end{Bmatrix} \quad (16)$$

Referring to FIG. 2, the pressure and/or pressure-volume loop at one or more components of the heart are determined from the personalized LPH model in act 26. After or as part of personalization, the pressure over time is calculated using the personalized parameters. The LPH model outputs the pressure-volume information given the personalized parameters. A patient-specific pressure for the heart chambers, at valves, and/or other locations is provided for the patient based on the LPH model.

In act 32, the model system of the medical system quantifies a hemodynamic parameter with computation flow dynamics using the three-dimensional representation and using the LPH for boundary conditions. In the left heart embodiment, the anatomical model 68 or geometry of the left heart is used as a spatial boundary condition. Pressure information from the LPH model 13 is used as another boundary condition. CFD is used to calculate the hemodynamics in any part of the heart given these boundary conditions. The 3D CFD model system solves for the hemodynamics of the heart of the patient. The 3D CFD model 15 is personalized by the 3D geometry for the patient and the pressure or pressures from the personalized LPH model 13 for the patient. Additional, different, or fewer parameters may be provided by the LPH model 13 for solving by the 3D CFD model 15.

Any hemodynamic parameter may be quantified. For example, the 3D CFD solves for a pressure, velocity, or pressure and velocity field over three dimensions. The biomarkers, which may be related with such pressure and/or velocity information, indicate performance of the heart. The 3D CFD model 15 allows computation of the hemodynamics at any location, such as at each of a plurality of locations within the heart in a regular 3D grid or along tissue (e.g., heart wall and/or valve leaflets).

The 3D CFD model 15 quantifies hemodynamics using the Navier-Stokes partial differential equations. Example Navier-Stokes equations are:

$$\rho \left( \frac{\partial u}{\partial t} + u \cdot \nabla u \right) = -\nabla p + \mu \Delta u + F \quad (17)$$

$$\nabla \cdot u = 0$$

The 3D Navier-Stokes equations describe the momentum and mass conservation for fluid flow inside the heart and are supplied by boundary conditions using a 1-way fluid-structure interaction (FSI) strategy. This strategy includes computing the boundary velocities from cardiac wall segmented kinematics, and imposing the boundary velocities as velocity boundary conditions for the Navier-Stokes equations. For example, a uniform grid discretization of a box-shaped domain enclosing the heart geometry is used. A level set representation of the cardiac walls, an "embedded boundary method," is used. The unknowns to be solved are the time-varying velocity vector field u and pressure scalar field p, at each point in the 3D computational domain. The blood is modeled as a Newtonian fluid due to the high-shear regime inside the left ventricle. The density and dynamic viscosity of the blood are set to generic mean values across healthy individuals (e.g. $\rho=1.06$ g/cm$^3$ and dynamic viscosity $\mu=3.5$ mPa·s), but other values may be used. The equations are solved numerically, for example by using the fractional step combined with an approximate projection method for the pressure. Other approaches may be used. Modeling the 3D+time fluid dynamics can be alternatively done with the Lattice-Boltzmann method (LBM) or other approaches. Various numerical discretization approaches, like the finite element method (FEM), immersed boundary method (IBM), or others may be used.

Figure 7:
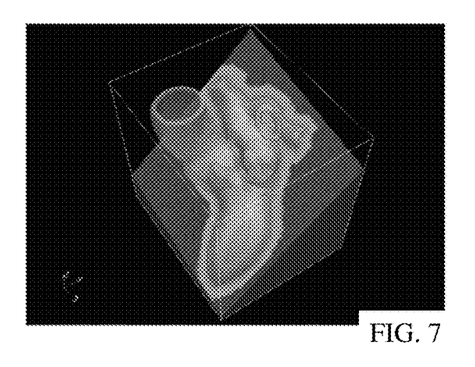
FIG. 7 shows an example image of embedding a heart model as a level set in a rectangular domain.

FIG. 7 shows an example of embedding the heart model as a level set in a rectangular domain. The transparent zero level corresponds to the thickened heart walls. FIG. 7 shows a cross-section color-coded based on the level set value. The darker values are positive, and lighter values are negative.

Figure 8:
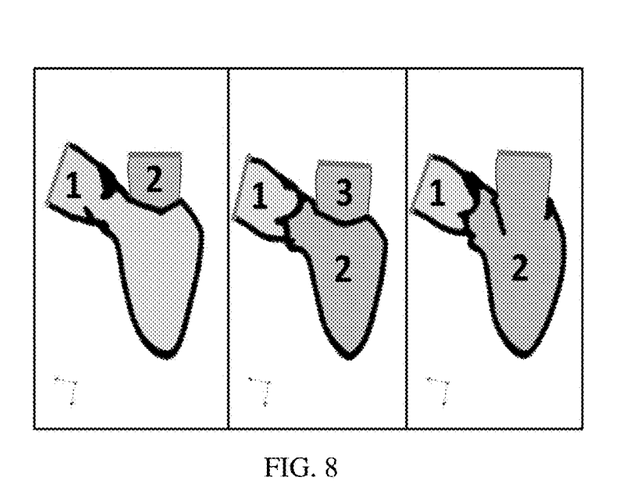
FIG. 8 shows three example phases associated with isovolumic operation.

This level set in the rectangular domain approach may be improved or altered. The fluid domain is defined explicitly (e.g. using FEM unstructured grids) or implicitly (e.g. with the use of a level set that separates the fluid region from the solid region, as shown in FIGS. 7 and 8). In one such geometric setup (FIG. 7), a heart mesh includes the endocardium. A rectangular (box) is defined to extend the computational domain such that the box fully encloses the mesh. A level set representation of the mesh (e.g. a signed-distance to the mesh) is computed in order to implicitly embed the mesh inside the domain.

The pressure over time is used as a boundary condition for the solution at the computational domain boundaries. The quantification applies the pressure over time from the LPH model 13 as the boundary condition, in addition to the boundary condition of the anatomical model 68 or mesh. For example, the aortic pressure over time is provided as a boundary condition at the aortic vessel boundary of the anatomical mesh, and the atrial pressure over time is provided as a boundary condition at the mitral rim boundary. The LPH model 13 communicates the pressure information to the 3D CFD model 15 of the medical system to be used as the boundary condition.

Figure 9:
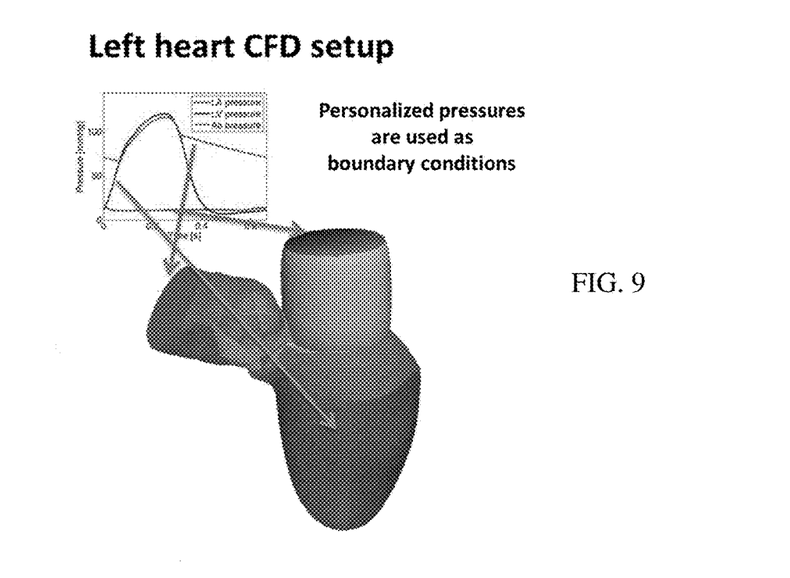
FIG. 9 shows an example computational flow dynamic model with personalized pressure information from the lumped-parameter model as boundary conditions.

FIGS. 8 and 9 show that the geometric model is endowed with "virtual" boundaries (inlets or outlets) at the aortic and atrial caps. The aortic vessel is capped distally, and the cap tagged as a "virtual boundary," on which one imposes Dirichlet boundary conditions on the pressure. The mitral rim is either capped directly (e.g. by performing a Delaunay triangulation of the mitral ring) or is extended away from the ventricle, for example as an extruded cylindrical mesh, along a direction normal to the mitral ring plane, to form a surrogate atrium, whose top is capped. This capped boundary zone is also used to impose Dirichlet boundary conditions on the pressure field.

The velocities obtained from the heart (e.g., Lagrangian) mesh provide Dirichlet boundary conditions to the N-S equations at any time t. On any of the virtual boundaries, the Dirichlet boundary conditions for the pressure at each point x are specified such that, for example, $p(x,t) - v \partial_n (u(x,t) \cdot n) = P(t)$ is enforced, given the normal direction to the cap surface denoted with n and for any tangential direction $\tau$ that $\partial_n (u(x,t) \cdot \tau) = 0$. Here $v$ is the kinematic viscosity of the blood, and P(t) is the prescribed boundary pressure, specified for each virtual boundary, in time t. The LPH model 13 provides the values of P over time. This can be done in at least two ways. In a first way, a decoupled (one-way) formulation is used. A full LPH computation is performed, and the LPH pressure values for the artery and atrium over time are imposed as the pressures come from LPH (this is illustrated by FIG. 9). In the second way, a coupled (two-way) formulation is used. The 3D CFD and LPH models 13, 15 are run synchronously. A feedback loop is provided between the LPH and the 3D solver code (i.e., 3D CFD model 15). At each time step, the values of the LPH pressure are computed using the current flow through the respective cap surface, while the 3D flow through one cap surface (e.g. arterial) depends both on the ventricular volume change, as well as on the flow through the other cap surface (e.g. atrial). If there are no regurgitations, the two ways are equivalent, but if a patient has regurgitations, there may be variation between the ways.

Pressure information loss during the isovolumic phases may be addressed in act 34. Pressure information loss occurs due to the topology changes in the computational domain showcased in FIG. 8. The computational domain changes the number of connected components from 2 to 3 and back to 2 during the cardiac cycle (e.g., moving from the left (systole for leftmost image), to the isovolumic relaxation (middle image) and then to diastole (rightmost image)). At any time, in case of no regurgitations, the pressure is at very different levels inside the various compartments (1, 2, 3) separated by a closed valve. For example during systole (left image), pressure values may rise to 120 mmHg in compartment 1, while staying at 10 mmHg in compartment 2. Similar pressure jumps between compartments are illustrated in the other two images. While the situation is a common occurrence in cardiac 3D CFD, the above level set solution of the Navier-Stokes for 3D CFD does not address how to handle compartmental pressure jumps as one transitions to (or from) an isovolumic phase from (or to) systole or diastole.

Mathematically and numerically, once the isovolumic phase is reached, the 3D pressure solver computing the pressure field inside the closed ventricle (compartment 2 in the isovolumic relaxation) has to solve a Poisson equation with Neumann boundary conditions. The Poisson equation with Neumann boundary conditions solution is unique only up to an undetermined constant of integration. This constant of integration is not continuous over time, and cannot produce temporally-consistent pressure fields across the whole domain. Using the LV pressure curve from the LPH model in act 34 constrains the integration constant in the Poisson solver during the isovolumetric stages, providing temporally-consistent fields. The constraint $$\int_{LV} p(x, t) = P$$

is imposed. The mean pressure inside the LV at time t during isovolumetric contraction or relaxation is thus imposed to be equal to the pressure value P(t) computed by the LPH model. This constraint ensures that the mean ventricular pressure follows the smooth curve computed by the LPH model 13. This constraint may be implemented by adding the constant value $$k(t) = P(t) - \int_{LV} p(x, t)$$

to all the LV points at a given time t, such that the new LV mean matches P(t), the LPH value of the LV pressure at time t. The Poisson equation is solved with Neumann boundary conditions if there are no regurgitations, and with mixed Dirichlet and Neumann boundary conditions if there are regurgitations, or during the main cardiac cycles (systole, diastole). Other implementations of the mean pressure constraint may be used.

In other embodiments, pressure boundary conditions are imposed at other locations with or without extending the mesh. For example, pressure boundary conditions for the 3D solver are imposed on the mitral zone (e.g., any cap surface bounded by the mitral ring). As another example, pressure boundary conditions are imposed for the 3D solver on the pulmonary vein caps.

The quantification by the 3D CFD model provides a three-dimensional distribution of the hemodynamic parameters for part or all of the heart. Since a grid is used, the pressure, flow, or other hemodynamic parameter for each location in the grid may be calculated. A field or distribution over three dimensions of pressure or velocity is determined. For example, the pressure at each side of the valves or along the heart walls is quantified. As another example, pressure variation is quantified. Due to the use of the LPH model-based pressures as a boundary constraint, the hemodynamic parameters are quantified as temporally-consistent, such as a temporally consistent pressure field during an isovolumic phase.

In act 38, a metric or metrics are indicated on a display. The metric may be a value, graph, vector field, or spatial distribution. The metric is displayed on a screen, such as displaying the pressure for a user selected location or pressure as a function of location. Other displays may be provided, such as indicating a workflow or providing instructions based on the metric. In alternative embodiments, the metric is stored in the patient record (e.g., memory) and/or transmitted on a computer network.

The metric is the hemodynamic parameter or information derived from the hemodynamic parameter. For example, the pressure values are displayed. The metric may be derived as a function of the hemodynamic parameter. For example, a map of range of pressure variation or pressure gradient is displayed. Other information may be displayed with the metric, such as overlaying color mapped from the metric onto a grayscale image from the scan data.

In one embodiment, the metric is an apical residence time derived from the hemodynamic parameter. This metric refers to the time spent by a particle or a set of blood particles in a certain cardiac region (ventricular apex in this instance), and characterizes the circulation efficiency of the ventricle as a pump. A longer residence time is usually thought to increase probability of blood clot formation. Other metrics may be calculated.

Figure 10:
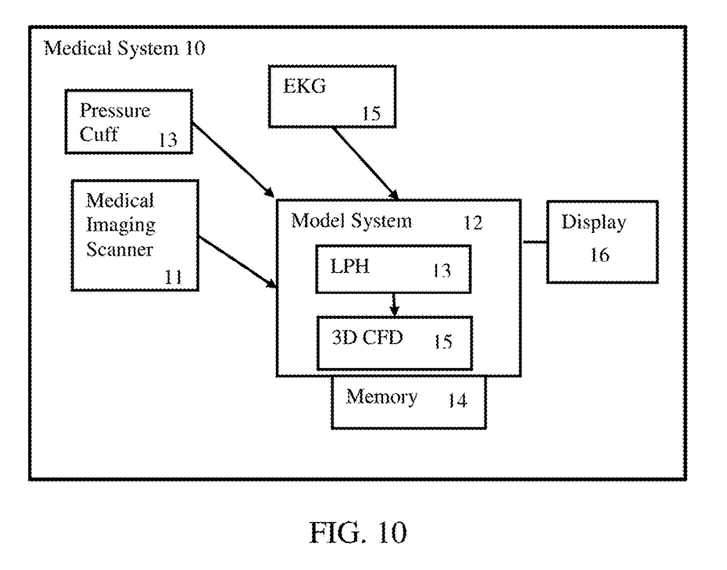
FIG. 10 is a block diagram of one embodiment of a system for three-dimensional hemodynamic quantification in a medical system.

FIG. 10 shows a medical system 10 for three-dimensional hemodynamic quantification. The medical system 10 includes a medical imaging scanner 11, a model system 12, a pressure cuff 13, a memory 14, an EKG sensor 15, and a display 16. The model system 12 may be implemented by a processor or other computer. The model system 12 and the memory 14 are shown separate from the medical imaging scanner 11, such associated with being a computer or workstation apart from the medical imaging scanner 11. In other embodiments, the model system 12 and/or memory 14 are part of the medical imaging scanner 11. In alternative embodiments, the medical system 10 is a workstation, computer, or server for computing values of metrics from data acquired by a separate system in real-time or using previously acquired patient-specific data stored in the memory 14. For example, the medical imaging scanner 11 is provided for acquiring data representing a volume, and a separate database, server, workstation, and/or computer is provided for personalizing and computing.

Additional, different, or fewer components may be used. For example, other sensors are used to gather patient-specific data. The pressure cuff 13 and/or EKG sensor 15 may or may not be used in other embodiments.

The computing components, devices, or machines of the medical system 10, such as the medical imaging scanner 11 and/or the model system 12 are configured by hardware, software, and/or design to perform calculations or other acts. The computing components operate independently or in conjunction with each other to perform any given act, such as the acts of FIG. 2 or 3. The acts are performed by one of the computer components, another of the computing components, or a combination of the computing components. Other components may be used or controlled by the computing components to scan or perform other functions.

The medical imaging scanner 11 is any now known or later developed modality for scanning a patient. The medical imaging scanner 11 scans the patient for a heart region. For example, a C-arm x-ray system (e.g., DynaCT from Siemens), CT like system, or CT system is used. Other modalities include MR, x-ray, angiography, fluoroscopy, PET, SPECT, or ultrasound. The medical imaging scanner 11 is configured to acquire the medical imaging data representing part or all of the heart. Data representing one or more vessels may be acquired. The data is acquired by scanning the patient using transmission by the scanner and/or by receiving signals from the patient. The type or mode of scanning may result in receiving data of just part of the cardiovascular system. For example, transthoracic scanning in ultrasound may scan the entire heart or part of the heart as limited by the acoustic window. Alternatively, data of a volume region is received and the heart information is segmented from information of other anatomy.

In one embodiment, the medical imaging scanner 11 is an ultrasound scanner. Acoustic energy is used to scan the heart. Tissue response is measured using B-mode scanning. Flow response is measured using flow or color Doppler scanning. Both tissue and flow response may be measured at similar times, such as interleaving the scanning of both modes by scan line, group of scan lines, or frame. The scanning is 4D or 3D+t. A volume is scanned.

The pressure cuff 13 is an automated or manual pressure detector. The cuff 13 is adapted for sensing pressure on an arm of the patient, but may sense pressure at other locations. In alternative embodiments, other pressure sensors may be used, such as a pressure sensor on a catheter inserted within the patient.

The EKG sensor 15 is a plurality of electrodes connected with a circuit or processor. An EKG waveform, heart rate, and/or phase designators sensed from the electrical signals are output by the EKG sensor 15.

The memory 14 is a buffer, cache, RAM, removable media, hard drive, magnetic, optical, database, or other now known or later developed memory. The memory 14 is a single device or group of two or more devices. The memory 14 is within the scanner 11, part of a computer with the model system 12, or is outside or remote from other components.

The memory 14 stores the clinical measurements of the patient (e.g., measurements from the pressure cuff 13 or the EKG sensor 15), other patient information, scan data (e.g., spatial anatomy or tissue data and/or flow data), models, values of parameters, values of personalized parameters, calculated quantities, and/or other information. The memory 14 stores data resulting from or used in the processes described herein, such as storing the constants, initial values, intermediate values, personalized values, computed metrics, or other properties. The storage may be transitory, such as associated with a buffer, or may be for long term, such as associated with a patient medical record.

The memory 14 is additionally or alternatively a non-transitory computer readable storage medium with processing instructions. The memory 14 stores data representing instructions executable by the programmed processor 12 for three-dimensional hemodynamic quantification in the medical system 10. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The model system 12 includes the LPH model 13 and the 3D CFD model 15. Additional, different, or fewer models may be included, such as also including an anatomy or heart model 68 (e.g., see FIG. 1). Each model 13, 15 is a different part of the model system 12. The different parts communicate, such as the LPH model 13 passing pressure curves or PV loop information to the 3D CFD model 15. The communication may be through shared access to a memory location or buffer. Alternatively, the communication is by transmission over a buss or network. Other communication may be used. The model system 12 is configured by software, hardware, and/or firmware.

The model system 12 is configured to segment heart geometry, fit the lumped-parameter model 13 to the heart of the patient with measurements from the segmented heart geometry, the clinical measurements, and flow measurements from the scan, and compute a biomarker (e.g., pressure, velocity, or derived value) quantity with a three-dimensional computed flow dynamics model 15 with the segmented heart geometry and information from the fit lumped-parameter model 13 as boundary conditions.

The model system 12 is implemented on one or more processors or other computing components. The model system 12 is code structures or representations of the heart and/or other cardiac parts. Any processor may be used, such as a general processor, digital signal processor, three-dimensional data processor, graphics processing unit, application specific integrated circuit, field programmable gate array, digital circuit, analog circuit, combinations thereof, or other now known or later developed device for modeling from medical data. The image processor implementing the model system 12 is a single device, a plurality of devices, or a network. For more than one device, parallel or sequential division of processing may be used. Different devices making up the image processor may perform different functions, such as personalizing by one device and computation of a metric by another device. In one embodiment, the image processor is a control processor or other processor of the medical imaging scanner 11. The processor operates pursuant to stored instructions to perform various acts described herein.

The display 16 is a CRT, LCD, plasma, projector, printer, or other output device for showing an image. The display 16 displays the quantity or quantities calculated using the model system 12. The quantities include the pressure field, velocity field, or biomarkers derived from the pressure and/or velocity fields. The 3D CFD model 15 provides the quantities or information used to calculate further quantities. Quantities from the LPH model 13 may be displayed. The quantities may be displayed in a chart, graph, and/or on an image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for three-dimensional hemodynamic quantification in a medical system, the method comprising:
capturing cardiovascular spatial data and flow data of a heart of a patient with a medical scanner of the medical system, the spatial and flow data representing a three-dimensional volume;
measuring pressure data of the patient with a pressure sensor of the medical system;
generating a three-dimensional representation of a portion of the heart from the spatial data;
estimating flow across valves of the heart from the flow data;
personalizing a lumped-parameter hemodynamics model representing at least the portion of the heart of the patient, the personalizing using the spatial data, the flow across the valves, and the pressure data, wherein personalizing the lumped-parameter hemodynamics model comprises calculating mean arterial pressure from the pressure data, calculating ejection fraction and end-diastolic volume from the spatial data, calculating values for a first sub-set of parameters of the lumped-parameter hemodynamics model from the mean arterial pressure, ejection fraction, and end-diastolic volume, and calibrating a second sub-set of the parameters of the lumped-parameter hemodynamics model with an optimization algorithm;
quantifying a hemodynamic parameter from computational flow dynamics using the three-dimensional representation and using the lumped-parameter hemodynamics model for a boundary condition, the quantifying providing a three-dimensional distribution of the hemodynamic parameter for the portion of the heart; and
indicating a metric on a display for the patient, the metric being a function of the quantifying of the hemodynamic parameter.

2. The method of claim 1 wherein capturing the cardiovascular spatial data and the flow data comprises capturing ultrasound data of the heart with the medical scanner comprising an ultrasound scanner.

3. The method of claim 1 wherein measuring the pressure data comprises measuring with a pressure cuff.

4. The method of claim 1 wherein generating the three-dimensional representation comprises segmenting the portion of the heart as represented in the cardiovascular spatial data.

5. The method of claim 1 wherein generating the three-dimensional representation comprises separately segmenting different parts of a left heart of the heart and fusing the different parts together into a mesh for the portion of the heart.

6. The method of claim 1 wherein estimating the flow comprises estimating the flow across regions detected in the spatial data for an atrial valve and a mitral valve, the flow calculated from the flow data for the regions.

7. The method of claim 1 wherein personalizing the lumped-parameter hemodynamics model comprises personalizing pulmonary circulation as a pulmonary resistance and compliance with the flow data, personalizing a time varying elastance model for heart chamber flow with volume over time from the spatial data and velocity from the flow data, personalizing valve resistance and inertance from the flow data, and personalizing systemic circulation with a Windkessel model.

8. The method of claim 1 further comprising determining a pressure-volume loop from the personalized lumped-parameters hemodynamics model, and wherein quantifying comprises constraining an integration constant as a function of the pressure-volume loop.

9. The method of claim 1 further comprising determining pressure over time from the personalized lumped-parameters hemodynamics model, and wherein quantifying comprises quantifying with the pressure over time as the boundary condition.

10. The method of claim 1 wherein quantifying comprises quantifying the hemodynamic parameter as temporally-consistent pressure field during an iso-volumic phase.

11. The method of claim 1 wherein quantifying comprises quantifying with Navier-Stokes equations with finite element modeling.

12. The method of claim 1 wherein quantifying comprises quantifying with aortic pressure over time from the lumped-parameter hemodynamics model as the boundary condition at an aortic vessel of the three-dimensional representation, and with atrial pressure over time from the lumped-parameter hemodynamics model as the boundary condition at a mitral rim.

13. The method of claim 1 wherein quantifying comprises calculating pressures along tissue as the three-dimensional distribution.

14. The method of claim 1 wherein quantifying comprises calculating pressure, velocity, or pressure and velocity fields.

15. The method of claim 1 wherein indicating the metric comprises indicating an apical residence time derived from the hemodynamic parameter.

16. The method of claim 1 wherein personalizing comprises personalizing with the lumped-parameter hemodynamics model representing one or more chambers and one or more valves.

17. The method of claim 16 wherein personalizing comprises personalizing with a change in volume of the one or more chambers being a difference in out and in flow rates and resistance and inertance of the one or more valves being a function of a difference in out and in pressures.

18. The method of claim 16 wherein personalizing comprises personalizing with the lumped-parameter hemodynamics model representing systemic circulation separately from the one or more chambers and the one or more valves.

19. The method of claim 1 wherein quantifying comprises constraining an integration constant in a Poisson solver during isovolumetric stages with a pressure from the lumped-parameter hemodynamics model.

* * * * *